(12) United States Patent
Burke

(10) Patent No.: US 8,405,508 B2
(45) Date of Patent: Mar. 26, 2013

(54) USE OF GAMMA HARDENED RFID TAGS IN PHARMACEUTICAL DEVICES

(75) Inventor: Aaron Burke, Hamilton, MA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 11/501,446

(22) Filed: Aug. 9, 2006

(65) Prior Publication Data

US 2008/0042837 A1   Feb. 21, 2008

(51) Int. Cl.
  *G08B 13/14* (2006.01)
  *H01L 21/00* (2006.01)
  *H01L 29/82* (2006.01)
  *A61L 2/00* (2006.01)

(52) U.S. Cl. ........... 340/572.1; 438/3; 438/57; 257/421; 422/22

(58) Field of Classification Search ............... 340/572.1
  See application file for complete search history.

(56) References Cited

U.S. PATENT DOCUMENTS

| | | | |
|---|---|---|---|
| 3,728,694 A | 4/1973 | Rohrer | 340/173.2 |
| 5,360,437 A | 11/1994 | Thompson | |
| 5,674,381 A | 10/1997 | Den Dekker | 210/85 |
| 5,866,907 A | 2/1999 | Drukier et al. | 250/366 |
| 5,892,706 A * | 4/1999 | Shimizu et al. | 365/145 |
| 5,923,001 A * | 7/1999 | Morris et al. | 177/245 |
| 6,032,543 A | 3/2000 | Arthun et al. | |
| 6,140,139 A * | 10/2000 | Lienau et al. | 438/3 |
| 6,285,285 B1 | 9/2001 | Mongrenier | |
| 6,366,206 B1 | 4/2002 | Ishikawa et al. | |
| 6,617,963 B1 | 9/2003 | Watters et al. | 340/10.41 |
| 6,717,154 B2 | 4/2004 | Black et al. | 250/393 |
| 6,779,575 B1 | 8/2004 | Arthun | |
| 6,795,339 B2 | 9/2004 | Ooishi | |
| 7,048,775 B2 | 5/2006 | Jornitz et al. | 95/1 |
| 8,028,835 B2 | 10/2011 | Yasuda et al. | |
| 8,111,159 B2 | 2/2012 | Andreasson et al. | |
| 2001/0007532 A1 | 7/2001 | Sato et al. | 365/173 |
| 2003/0072676 A1 * | 4/2003 | Fletcher-Haynes et al. | 422/23 |
| 2003/0156449 A1 | 8/2003 | Ooishi | |

(Continued)

FOREIGN PATENT DOCUMENTS

| | | |
|---|---|---|
| CN | 1201523 A | 12/1998 |
| CN | 1658233 A | 8/2005 |

(Continued)

OTHER PUBLICATIONS

European Search Report dated Mar. 3, 2010 in corresponding foreign application (EP08164914).

(Continued)

*Primary Examiner* — Wayne Young
*Assistant Examiner* — John Mortell
(74) *Attorney, Agent, or Firm* — Nields, Lemack & Frame, LLC

(57) ABSTRACT

A system and method for utilizing RFID tags in environments where radiation is used is disclosed. RFID tags are secured to various components of a pharmaceutical system, thereby enabling the customer to download pertinent information about the component, such as lot number, date of manufacturer, test parameters, etc. The tags can be applied to the component during or immediately after manufacture and can be subjected to the sterilization process without risk of data loss or corruption. The memory device within the tag utilizes a technology that does not rely upon charge storage as its mechanism to store information.

26 Claims, 1 Drawing Sheet

U.S. PATENT DOCUMENTS

| | | | |
|---|---|---|---|
| 2003/0164401 A1 | 9/2003 | Andreasson et al. | |
| 2003/0183699 A1* | 10/2003 | Masui | 235/492 |
| 2004/0173456 A1 | 9/2004 | Boos et al. | |
| 2005/0040433 A1 | 2/2005 | Nozieres et al. | |
| 2005/0132821 A1 | 6/2005 | Furey et al. | |
| 2005/0205658 A1 | 9/2005 | Baker et al. | 235/375 |
| 2005/0210302 A1 | 9/2005 | Kato et al. | |
| 2006/0016897 A1 | 1/2006 | Yasuda et al. | |
| 2006/0092013 A1 | 5/2006 | Hager et al. | |
| 2006/0201263 A1 | 9/2006 | Furey et al. | |
| 2006/0211995 A1 | 9/2006 | Myhrberg et al. | |
| 2006/0220868 A1 | 10/2006 | Takasawa et al. | |
| 2006/0272432 A1 | 12/2006 | Belongia | |
| 2007/0217717 A1 | 9/2007 | Murray | |
| 2008/0137399 A1* | 6/2008 | Chan et al. | 365/158 |
| 2012/0061463 A1 | 3/2012 | Burke | |

FOREIGN PATENT DOCUMENTS

| | | |
|---|---|---|
| CN | 1695161 A | 11/2005 |
| DE | 29819987 U1 | 1/1999 |
| EP | 1001265 A2 | 5/2000 |
| EP | 1754973 A2 | 2/2007 |
| GB | 1 325 961 | 8/1973 |
| GB | 1 527 341 A | 10/1978 |
| JP | 11-297963 A | 10/1999 |
| JP | 2003-243631 A | 8/2003 |
| JP | 2005-503669 A | 2/2005 |
| JP | 2005-503870 A | 2/2005 |
| JP | 2006-39773 A | 2/2006 |
| WO | 96/14043 A1 | 5/1996 |
| WO | 97/16715 A1 | 5/1997 |
| WO | 01/47466 A1 | 7/2001 |
| WO | 03/026724 A1 | 4/2003 |
| WO | 2004/023389 A2 | 3/2004 |
| WO | 2004/028631 A1 | 4/2004 |
| WO | 2006/032326 A1 | 3/2006 |
| WO | 2006/041965 A2 | 4/2006 |

OTHER PUBLICATIONS

Japanese communication dated May 25, 2010 in corresponding foreign application (JP2007-206746).
Chinese Communication issued Mar. 6, 2009 in corresponding Chinese patent application No. 200710140715.7.
Chinese Communication issued Dec. 11, 2009 in corresponding Chinese patent application No. 200710140715.7.
Chinese Communication issued May 7, 2010 in corresponding Chinese patent application No. 200710140715.7.
Notice of Opposition to a European Patent, dated Sep. 16, 2009, European Patent No. 1887581 (formerly corresponding EP patent app No. EP 07253109.8/), filed in the name of NewAge Industries, Inc., 28 pages.
Opposition Letter to European Patent, dated Oct. 7, 2010, European Patent No. 1887581 (formerly corresponding EP patent app No. EP 07253109.8/), filed in the name of NewAge Industries, Inc., 8 pages.
European Communication dated Sep. 19, 2011 in corresponding European patent application No. EP 07253109.
RFID Update: The RFID Industry Daily, Dec. 13, 2006, Online article "New RFID Tag Withstands Industrial Sterilization", http://www.rfidupdate.com/articles/index.php?id=1261, accessed Mar. 18, 2009, 2 pages.
AdvantaPure, Newage Industries, GammaTag: Gamma Sterilizable RFID Tags Product Information Sheet, Mar. 17, 2008, www.gammatag.com, 2 pages.
VH&S Internal Memo, "Total Dose Radiation Tests at FRAM Non-Volatile Memories", RAMTRON TID NOBias.PDF (published prior to Apr. 2, 2005, see OLD, NASA Office of Logic Design), 4 pages.
Ramtron SPROM Heavy Ion Test, BNL, Nov. 1998, last revised Jan. 9, 2002, accessed Mar. 14, 2008, http://klabs.org/richcontent/MemoryContent/FRAM/FRAM_SPRO . . . , "Ramtron Serial FRAM Heavy Ion Test", Programmable Technologies Web Site/A scientific study of the problems of digital engineering for space fight systems, with a view to their practical solution, 2 pages, Katz.
Ramtron International Corporation, AN-200, "Advantages of the FM24C16/Serial 16Kb FRAM Memory", Jan. 1999, 2 pages.
Beacon eSpace at NASA Jet Propulsion Laboratory, California Institute of Technology, http://trs-new.jpl.nasa.gov/dspace/handle/2010/13434, Nov. 7, 2001, Nonvolatile Memory Workshop, San Diego, CA, JPL TRS 1992+, "Radiation response of emerging FeRAM technology", 6 pages, Nguyen, et al.
Celis Technology, Celis Semiconductor, White Papers, http://www.celis-semi.com/Technology/Technology_white%20papers.htm, Jet Propulsion Laboratory MRQ Conference, Oct. 1999, 6 pages, "Reliability of Ferroelectric Memory for High-Rel and Space Applications", Philpy, et al.
Beacon eSpace at NASA Jet Propulsion Laboratory, California Institute of Technology, http://trs-new.jpl.nasa.gov/dspace/handle/2014/10677, Nov. 4, 2002, Nonvolatile Memory Technology Symposium 2002, Honolulu, HI, JPL TRS 1992+, "Reliability and endurance of FRAM: a case study", 6 pages, Namkung, et al.
Nasa Office of Logic Design (OLD), A scientific study of the problems of digital engineering for space flight systems, with a view to their practical solution, "Memories: Radiation Test Results", last revised Apr. 2, 2005, http://klabs.org/richcontent/MemoryContent/mem_pages/mem_rad_res . . . , accessed Mar. 14, 2008, 6 pages.
Ramtron International Corporation, Technical Paper, May 2005, 3 pages, "The Endurance Performance of 0.5um FRAM Products", Chu, et al.
Non-Volatile Memory Technology Symposium, Nov. 2000, Advances in FeRAM Technology Slide presentation, 23 pages, Derbenwick, et al.
News Release of RFID International Business Association, et al., Feb. 28, 2006, "RFID Accredited Workshop Added to INTERPHEX2006 Pre-Conference Program/Recent FDA Symposium Exposes Importance of RFID Education", 3 pages.
EE Times India, Aug. 12, 2005, www.eetindia.co.in/ART, "RF Wireless Design, RFID Tag with 256 bytes of FRAM", 1 page.
Business Wire, Dec. 10, 2003, www.thefreelibrary.com/_/print/PrintArticle.aspx?id=111091130, "RF SAW, Inc. Announces Gamma Radiation Hard RFID Tags; Doses Up to 5 Mega Rads—500 Million Ergs/Gm—With No Measurable Degradation", 1 page.
J. Appl. Phys. 66 (3), Aug. 1, 1989, pp. 1444-1453, "Radiation effects on ferroelectric thin-film memories: Retention failure mechanisms", Scott, et al.
Electronic News, Jun. 6, 1994, 2 pages, "Motorola signs ferroelectric RAM deal", Krause.
Fujitsu Microelectronics America, Inc. News Release, Aug. 9, 2005, www.fujitsu.com/us/news/pr/fma_20050809.html, 2 pages, "Fujitsu Introduces New, Light, Cost-Effective RFID Tags with 256 Bytes of FRAM for Product Tracking, Distribution Applications".
Patient Safety, Apr. 26, 2006, 1 page, http://medicalconnectivity.com/2006/04/26/could-saw-rfid-tags-serv . . . , "Could SAW RFID Tags Serve Health Care?", Gee.
IEEE Circuits & Devices, Jan. 2001, pp. 20-30, "Ferroelectric Memory: On the Brink of Breaking Through", Derbenwick, et al.
IEEE Transactions on Nuclear Science, vol. 41, No. 3, Jun. 1994, pp. 495-502, "A Study of Radiation Vulnerability of Ferroelectric Material and Devices", Coic, et al.
Fujitsu Limited News Release, Feb. 27, 2003, "Fujitsu Develops High Capacity, High Speed Chip with Embedded FRAM for RFID Tags", 3 pages.
IEEE Transactions on Nuclear Science, vol. 38, No. 6, Dec. 1991, pp. 1410-1414, "Radiation Evaluation of Commercial Ferroelectric Nonvolatile Memories", Benedetto, et al.
Escort Memory Systems Lead Sheet, Interphex Trade Show, NewAge-Advantapure discussions, Mar. 21, 2006 and May 10, 2006, 1 page.
NewAge Industries Purchase Order, Jul. 25, 2006, order of 2500 gamma radiation resistant RFID tags from EMS, 1 page.
David A. Kamp et al.; "Adaptable Ferroelectric Memories for Space Applications"; Cells Semiconductor Corporation—Abstract.
Ramtron Vendor Test Report.
Non-Volatile Memory Technology Symposium, Nov. 15-16, 2000, pp. 1-3, "Advances in FeRAM Technologies", Derbenwick, et al.

Non-Volatile Memory Technology Symposium, Nov. 15-16, 2000, Advances in FeRAM Technology Slide presentation, 23 pages, Derbenwick, et al.

Office Action mailed Aug. 29, 2012 in corresponding U.S. Appl. No. 13/301,871.

English translation of Japanese Communication dispatched Sep. 4, 2012 in corresponding Japanese patent application No. 2011-123696.

International Preliminary Report on Patentability received for PCT Patent Application No. PCT/US2008/008834, issued on Feb. 2, 2010, 7 pages.

International Search Report and Written Opinion received for PCT Patent Application No. PCT/US2008/008834, mailed Feb. 18, 2009, 8 pages.

Office Action mailed Oct. 24, 2012 in co-pending U.S. Appl. No. 12/452,747.

Chinese Communication, with English translation, issued Mar. 1, 2012 in corresponding Chinese Patent Application No. 201010227198.9.

Chinese communication dated May 7, 2010 in co-pending foreign application (2007-10140715.7).

CN communication dated Dec. 11, 2009.

Chinese communication dated Mar. 6, 2009.

\* cited by examiner

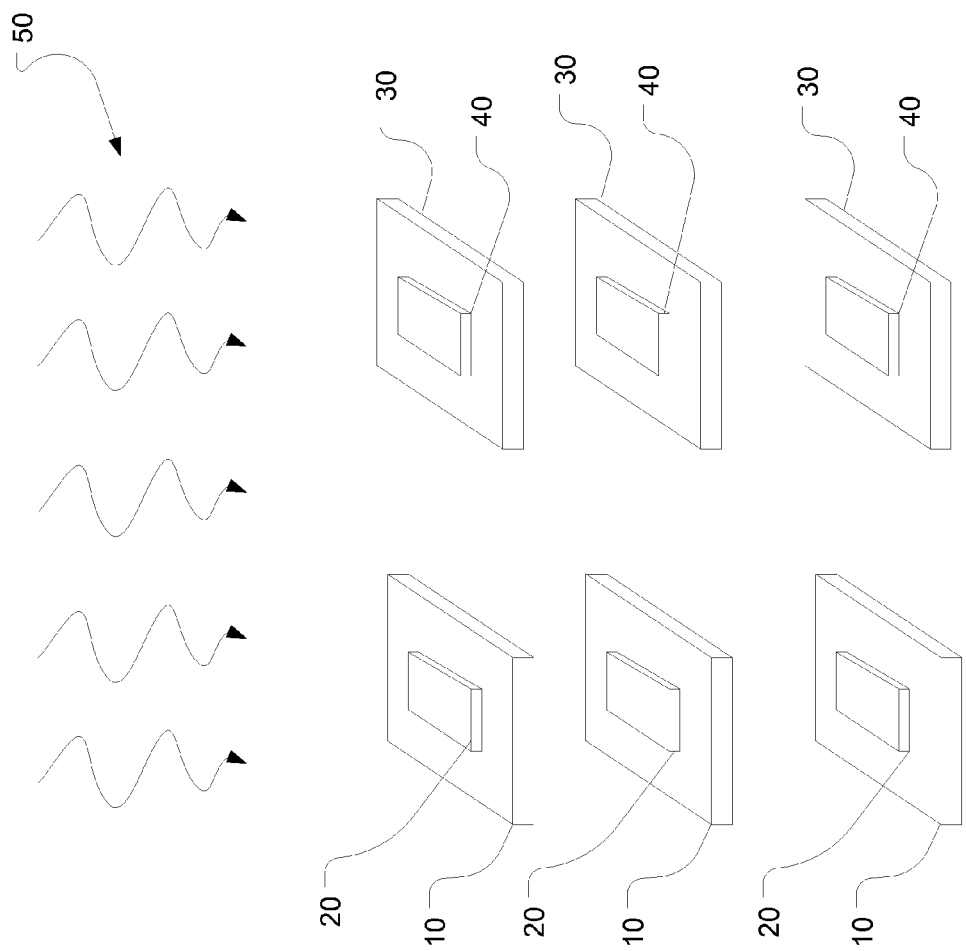

USE OF GAMMA HARDENED RFID TAGS IN PHARMACEUTICAL DEVICES

BACKGROUND OF THE INVENTION

The use of RFID tags has become prevalent, especially in the management of assets, particularly those applications associated with inventory management. For example, the use of RFID tags permits the monitoring of the production line and the movement of assets or components through the supply chain.

To further illustrate this concept, a manufacturing entity may adhere RFID tags to components as they enter the production facility. These components are then inserted into the production flow, forming sub-assemblies in combination with other components, and finally resulting in a finished product. The use of RFID tags allows the personnel within the manufacturing entity to track the movement of the specific component throughout the manufacturing process. It also allows the entity to be able to identify the specific components that comprise any particular assembly or finished product.

In addition, the use of RFID tags has also been advocated within the drug and pharmaceutical industries. In February 2004, the United States Food and Drug Administration issued a report advocating the use of RFID tags to label and monitor drugs. This is an attempt to provide pedigree and to limit the infiltration of counterfeit prescription drugs into the market and to consumers.

Since their introduction, RFID tags have been used in many applications, such as to identify and provide information for process control in filter products. U.S. Pat. No. 5,674,381, issued to Den Dekker in 1997, discloses the use of "electronic labels" in conjunction with filtering apparatus and replaceable filter assemblies. Specifically, the patent discloses a filter having an electronic label that has a read/write memory and an associated filtering apparatus that has readout means responsive to the label. The electronic label is adapted to count and store the actual operating hours of the replaceable filter. The filtering apparatus is adapted to allow use or refusal of the filter, based on this real-time number. The patent also discloses that the electronic label can be used to store identification information about the replaceable filter.

A patent application by Baker et al, published in 2005 as U.S. Patent Application Publication No. US2005/0205658, discloses a process equipment tracking system. This system includes the use of RFID tags in conjunction with process equipment. The RFID tag is described as capable of storing "at least one trackable event". These trackable events are enumerated as cleaning dates, and batch process dates. The publication also discloses an RFID reader that is connectable to a PC or an internet, where a process equipment database exists. This database contains multiple trackable events and can supply information useful in determining "a service life of the process equipment based on the accumulated data". The application includes the use of this type of system with a variety of process equipment, such as valves, pumps, filters, and ultraviolet lamps.

Another patent application, filed by Jornitz et al and published in 2004 as U.S. Patent Application Publication No. 2004/0256328, discloses a device and method for monitoring the integrity of filtering installations. This publication describes the use of filters containing an onboard memory chip and communications device, in conjunction with a filter housing. The filter housing acts as a monitoring and integrity tester. That application also discloses a set of steps to be used to insure the integrity of the filtering elements used in multi-round housings. These steps include querying the memory element to verify the type of filter that is being used, its limit data, and its production release data.

Despite the improvements that have occurred through the use of RFID tags, there are additional areas that have not been satisfactorily addressed. For example, to date, RFID tags cannot be employed in environments that require or utilize sterilization utilizing radiation. This is due to the fact that the memory storage devices within the RFID tag cannot withstand those types of radiation. When subjected to sterilization utilizing radiation, specifically gamma radiation, the contents of these memory elements are corrupted, thereby rendering them useless in this environment. However, there are a number of applications, such as, but not limited to, the drug and pharmaceutical industries, where sterilization utilizing radiation of the system is a requirement. Therefore, it would be extremely beneficial to these industries and others, to have an RFID tag which could withstand this type of radiation without data loss or corruption.

SUMMARY OF THE INVENTION

The shortcomings of the prior art are overcome by the present invention, which describes a system and method for utilizing RFID tags in environments where radiation is used. RFID tags are secured to various components of a pharmaceutical system, thereby enabling the customer to download pertinent information about the component, such as lot number, date of manufacturer, test parameters, etc. The tags can be applied to the component during manufacturing or immediately after the final assembly and can be subjected to the sterilization process without risk of data loss or corruption. The memory device within the tag utilizes a technology that does not rely upon charge storage as its mechanism to store information.

BRIEF DESCRIPTION OF THE DRAWINGS

FIG. 1 shows several RFID tags with a ferroelectric memory, in accordance with one embodiment of the disclosed invention, and several conventional RFID tags, each being subjected to gamma radiation.

DETAILED DESCRIPTION OF THE INVENTION

The use of RFID tags has become more and more prevalent. However, in certain applications, their use is limited, or not possible. For example, any environment in which the tag must be subjected to radiation will corrupt or destroy the contents of the memory device within the tag. Therefore, devices that are gamma irradiated, such as pharmaceutical components, or subject to x-rays, such as devices that pass through airport security systems, currently cannot utilize RFID tags. Thus, products used in these environments must find alternative solutions. For example, in some cases, a simple barcode is affixed to the device, and a database is used to store and retrieve the pertinent information associated with that barcode. In other words, the memory element of the tag is literally removed and kept elsewhere. While this allows the data associated with the device to be saved and retrieved, it requires computer access and a remote database for storage. This solution is further complicated when the device manufacturer and the device user both want to access and update the associated information. Such an arrangement requires joint access to the database, which may be difficult or impossible due to the need for confidentiality and data protection.

A second solution involves affixing the RFID tag at a point in the process after the irradiation of the device. For example, pharmaceutical components are often subjected to gamma radiation. Application of the RFID tag after this step can bypass the memory corruption issue. However, data associated with that component which was created before the radiation step must be somehow saved and associated with the appropriate component, so that the later affixed tag contains all of the required information.

A third solution is to prohibit the use of radiation with the device. Thus, users must find an alternate approach to achieve the results sought by irradiating the device (such as heat sterilization). Obviously, none of these solutions is optimal.

It should be noted that although the present application describes the use of RFID tags, the invention is not so limited. The fundamental issue to be solved is a limitation of the memory device used, and is not related to the particular communication protocol. Thus, while the memory devices within RFID tags clearly are affected by radiation, so too are devices which use memory devices with other communication protocols, such as Zigbee (IEEE 802.15.4), Bluetooth (IEEE 802.15.1), WiFi (IEEE 802.11), IrDA, and others.

At the root of the problem is the inability for a traditional memory device to withstand radiation. This is a very well known problem, and affects all types of memory, including FLASH, EEPROM, DRAM and SRAM. Since each of the aforementioned memory device utilizes stored charge to represent the value of each binary bit, each is susceptible to corruption caused by radiation. In this case, the charge stored in the capacitor is either depleted or enhanced by the radiation, thereby affecting its value.

There are other memory technologies that use mechanisms other than charge storage to retain the value of a bit. For example, FRAMs, or ferro-electric RAMs, utilize molecules having a bi-stable structure to store state, wherein one of the stable molecular configurations represents a '1', and the other stable configuration represents a '0'. Several common molecules used in FRAMs are PZT (lead-zirconate-titanate), SBT (strontium-bismuth-tantalate) and BLT (lanthanum substituted bismuth-tantalate). Each possesses a central atom in a cubic unit cell having a dipole moment. These molecules switch between these two stable states based on the application of an electric field to the molecule. Since these cells rely on electrical fields, rather than charge storage, memories utilizing this mechanism are far less susceptible to gamma and other types of radiation than traditional semiconductor memory structures. Ferro-electric devices are well known and are described in more detail in U.S. Pat. No. 3,728,694, issued to Rohrer.

Another example of a memory device that does not utilize charge as the storage mechanism is MRAM, also known as magnetoresistive or simply magnetic RAM. These memory devices utilize ferromagnetic material, often in the form of Hall sensors, to store the state of the bit. Further details are provided in U.S. Pat. No. 6,140,139. Since magnetic fields are utilized, rather than capacitive charge, these memory devices are also much less susceptible to gamma radiation.

As stated above, memory devices that do not utilize charge as the storage mechanism are less susceptible to corruption due to radiation, particularly gamma radiation, thereby making them particularly advantageous in certain applications. RFID and other remotely readable tags that must pass through x-ray machines, such as airport screening machines, or tags that are used in the pharmaceutical and drug industries, can function when assembled using these memory devices.

In one experiment, shown in FIG. 1, RFID tags 10 utilizing a ferroelectric memory device 20, and several tags 30 utilizing conventional memory technology 40, were subjected to repeated exposure of gamma radiation 50. Each was subjected to a standard 25 kGray dosage. Thereafter, each was read. All of the tags 30 utilizing the conventional memories 40 were unreadable, while those tags 10 utilizing the ferroelectric memory devices 20 were functional. A test pattern was then written to each of the functioning devices 10 and they were then subjected to a second dose of radiation 50. The tags were then retested and the test pattern was readable in each.

Based on this, it is possible to develop a sophisticated pharmaceutical asset management system. In one embodiment, the pharmaceutical components, such as filtration devices and the like, have a remotely readable tag affixed to them, such as an RFID tag. This tag contains device specific information, such as, but not limited to device specific information (such as serial number, date of manufacture, etc.), device specifications (such as upper and lower pressure limits), and device test parameters. Customers could use this information in a variety of ways. For example, an automated instrument setup and calibration procedure can be established. By using an RFID or equivalent reader, the customer could determine calibration values, upper and lower limits, units of measure and/or the data exchange protocol.

These tags can also be used in conjunction with remote sensors, such as pressure, temperature and concentration sensors. The use of these types of sensors is described in U.S. patent applications Ser. Nos. 11/402,737, 11/402,437, and 11/402,438, the disclosure of each is hereby incorporated by reference. In this case, information obtained by the sensors can be stored in the RFID tags and read by the customer at a later time.

Finally, the ability to utilize a remotely readable asset management tag is beneficial for pharmaceutical consumables, such as filters, bags, tubes and process instruments. Currently, the pharmaceutical industry is exploring the possibility of disposable technology. In this scenario, the customer could configure their required system using at least some disposable components (such as filters, bags, hoses, etc). This allows the customer to customize their configuration as necessary and also eliminates the costly cleaning operations that must currently be performed. To improve the efficiency and predictability of using disposable components, RFID tags can be affixed to these components. Such tags allow for the wireless automated identification of components, including such information as catalog number, serial number, and date of manufacture. These tags also allow a secure automated method of transferring unit specific specification to the customer as noted above. Using the information contained within these tags, a GAMP compliant method of transferring unit specific test procedure information to an automated integrity tester can be created. The memory devices described above are beneficial in this application, since these disposable components must be irradiated to insure sterilization.

What is claimed:

1. A method of sterilization by subjecting a device to gamma radiation, wherein said device comprises a remotely readable and rewriteable memory device, whereby the contents of said memory device are not corrupted by said gamma radiation, comprising:
   affixing a memory device employing a non-charge based storage mechanism to said device; writing data to said memory device; subjecting said device and said memory device to gamma radiation subsequent to writing said data; and reading said data previously written to said memory device subsequent to said gamma sterilization.

2. The method of claim 1 wherein said memory device comprises a ferro-electric memory device.

3. The method of claim 1 wherein said memory device comprises a magnetoresistive memory device.

4. The method of claim 1 wherein said device comprises an RFID tag, said tag comprising said remotely readable and rewriteable memory device.

5. The method of claim 1, wherein said device comprises a pharmaceutical component.

6. The method of claim 5, wherein said component is selected from the group consisting of filters, bags, tubes and process instruments.

7. The method of claim 1, wherein said device comprises wireless communication means.

8. The method of claim 7, wherein said means comprises RFID.

9. The method of claim 7, wherein said means comprises the communication protocol described in IEEE 802.15.4.

10. The method of claim 7, wherein said means comprises the communication protocol described in IEEE 802.15.1.

11. A pharmaceutical component, comprising a rewritable memory element affixed thereto, which when subjected to gamma radiation, retains the contents of said memory element, comprising a memory element utilizing a non-charge based storage mechanism.

12. The pharmaceutical component of claim 11, wherein said memory device comprises a ferroelectric memory.

13. The pharmaceutical component of claim 11, wherein said memory device comprises a magnetoresistive memory.

14. The pharmaceutical component of claim 11, wherein said component is selected from the group consisting of filters, bags, tubes and process instruments.

15. The pharmaceutical component of claim 11, further comprising wireless communication means.

16. The pharmaceutical component of claim 15, wherein said means comprises RFID.

17. The pharmaceutical component of claim 15, wherein said means comprises the communication protocol described in IEEE 802.15.4.

18. The pharmaceutical component of claim 15, wherein said means comprises the communication protocol described in IEEE 802.15.1.

19. The method of claim 1, wherein said data comprises device specific information.

20. The method of claim 19, wherein said device specific information is selected from the group consisting of serial number, date of manufacture, device specifications and device test parameters.

21. The method of claim 1, further comprising writing additional data to said device after subjecting said device and said memory device to said gamma sterilization.

22. The method of claim 19, further comprising establishing an automated instrument setup and calibration procedure based on said data read after subjecting said device and said memory device to gamma sterilization.

23. The method of claim 19, further comprising creating a unit specific test procedure based on said data read after subjecting said device and said memory device to gamma sterilization.

24. A tracking system for gamma radiated lots of sterilized items, comprising:
   a tracking tag comprising a rewritable memory device which, when subjected to gamma radiation, retains the contents of said memory device, said memory device comprising device specific information written thereto prior to said gamma radiation; and
   a memory reader which is usable by a user to obtain the device specific information from said memory device after it has been gamma radiated.

25. The system of claim 24, wherein said device specific information is selected from the group consisting of serial number, date of manufacture, device specifications and device test parameters.

26. The system of claim 24, wherein said memory device comprises a ferroelectric memory.

* * * * *